United States Patent [19]
Kuris et al.

[11] 3,980,906
[45] Sept. 14, 1976

[54] ULTRASONIC MOTOR-CONVERTER SYSTEMS

[75] Inventors: Arthur Kuris, Riverdale; Lewis Balamuth, Southampton; Manuel Karatjas, Glen Oaks, all of N.Y.

[73] Assignee: Xygiene, Inc., Panama, Panama

[22] Filed: Mar. 14, 1974

[21] Appl. No.: 451,174

Related U.S. Application Data

[62] Division of Ser. No. 318,428, Dec. 26, 1972, Pat. No. 3,828,770.

[52] U.S. Cl. ............................ 310/8.1; 15/32; 128/24 A; 128/62 A; 310/8.2; 310/8.3; 310/8.7; 318/116
[51] Int. Cl.² .................................. C07C 41/08
[58] Field of Search .............. 310/8.1, 8.2, 8.3, 8.7; 318/116, 118; 128/24 A, 62 A; 32/28, 50, 56, 58, 65, 66, DIG. 4; 15/32; 51/59 SS

[56] References Cited
UNITED STATES PATENTS

| | | | |
|---|---|---|---|
| 2,616,223 | 11/1952 | Jonker | 318/116 X |
| 2,848,672 | 8/1958 | Harris | 318/116 X |
| 2,991,400 | 7/1961 | Van Der Burgt | 318/118 |
| 3,152,295 | 10/1964 | Schebler | 318/118 |
| 3,335,443 | 8/1967 | Parisi et al. | 128/24 A |
| 3,351,539 | 11/1967 | Branson | 310/8.1 UX |
| 3,371,233 | 2/1968 | Cook | 318/118 X |
| 3,375,820 | 4/1968 | Kuris et al. | 128/62 A |
| 3,432,691 | 3/1969 | Shoh | 310/8.1 |
| 3,489,930 | 1/1970 | Shoh | 310/8.1 |
| 3,547,110 | 12/1970 | Balamuth | 128/24 A |
| 3,581,125 | 5/1971 | Arndt | 310/8.1 |
| 3,582,733 | 6/1971 | Brubaker | 318/116 |
| 3,584,244 | 6/1971 | Vest | 310/8.1 |
| 3,596,206 | 7/1971 | Loria | 310/8.1 X |
| 3,638,087 | 1/1972 | Ratcliff | 318/118 |
| 3,651,352 | 3/1972 | Puskas | 310/8.1 |

*Primary Examiner*—Mark O. Budd

[57] ABSTRACT

Ultrasonic systems for use in consumer, and other applications, having electromechanical motor systems providing bursts of ultrasonic mechanical vibration at an applicator repeated at a sonic frequency to produce both ultrasonic and sonic vibratory motion and effect during use of said applicator.

24 Claims, 23 Drawing Figures

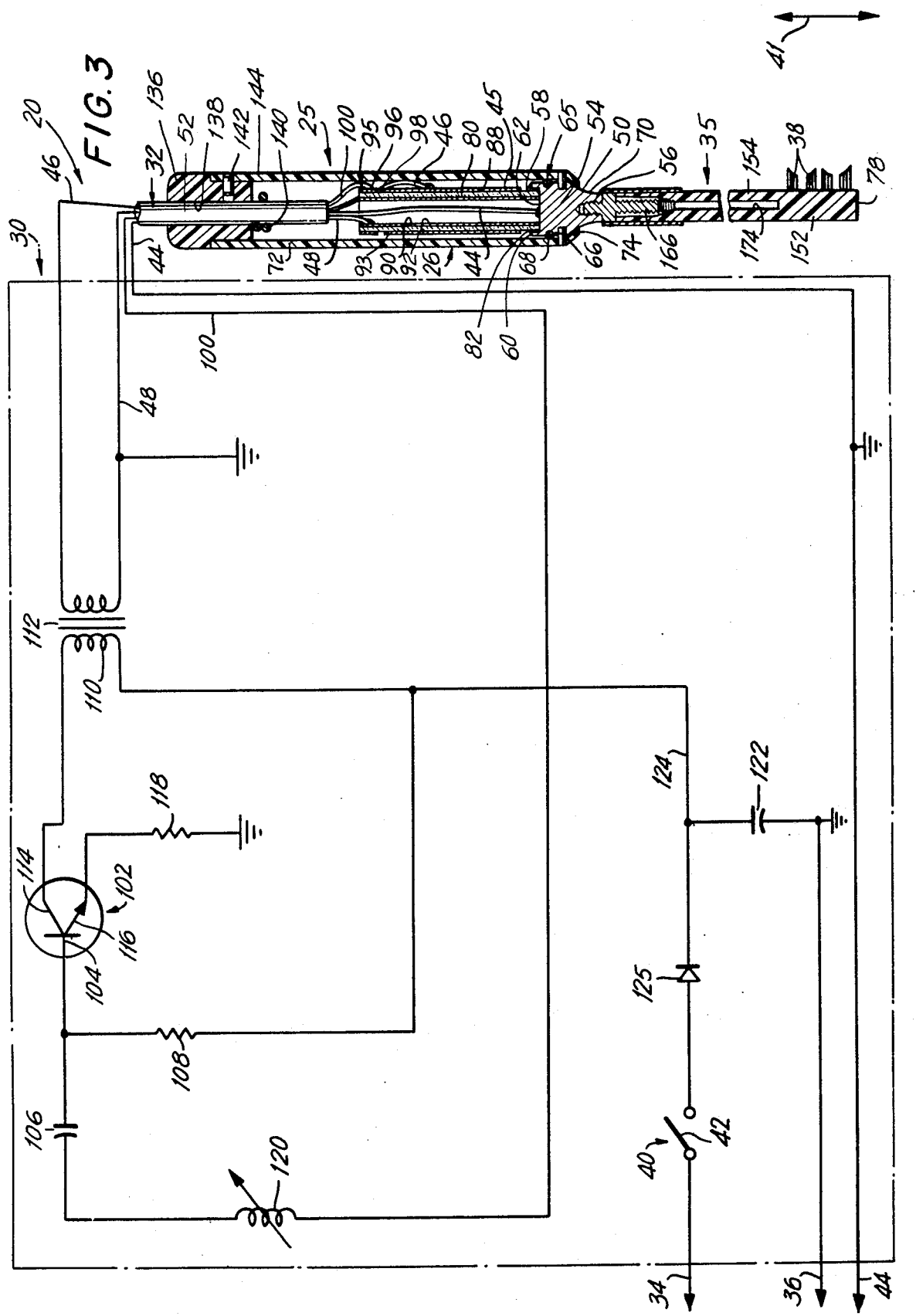

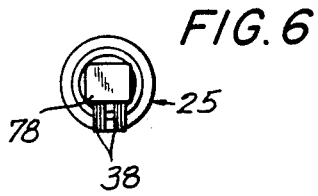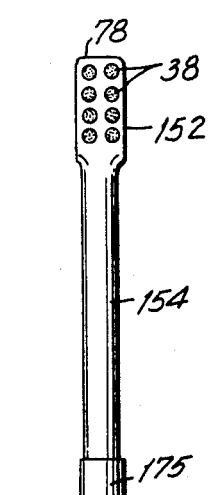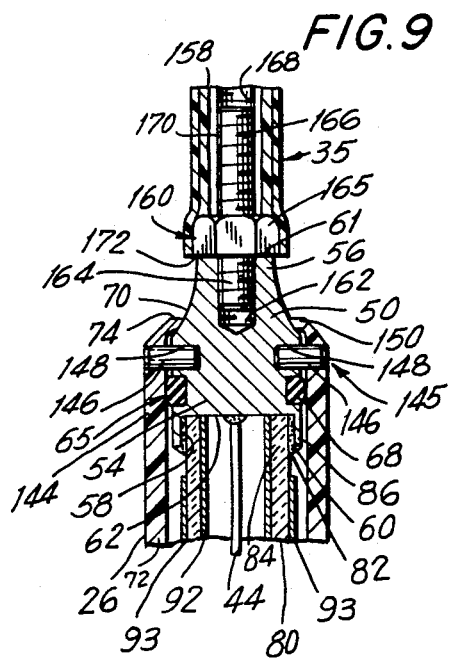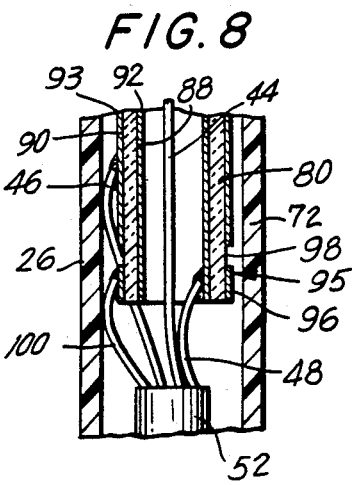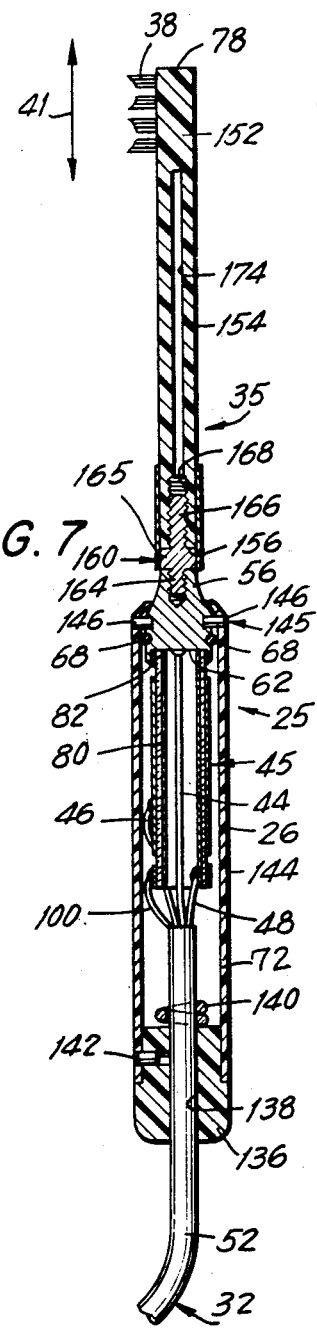

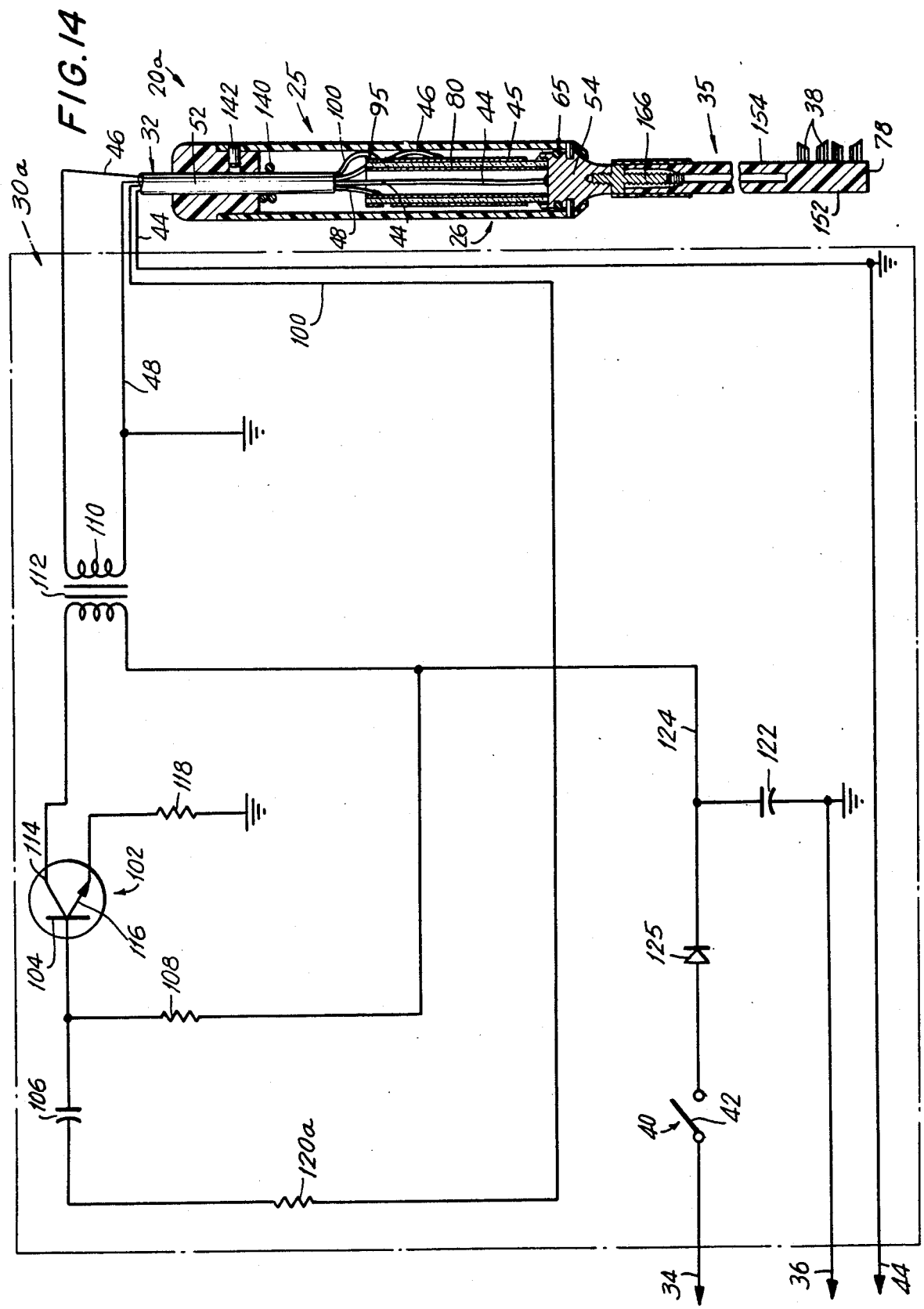

ULTRASONIC MOTOR-CONVERTER SYSTEMS

This is a continuation, division, of application Ser. No. 318,428 filed Dec. 26, 1972 now U.S. Pat. No. 3828770 issued 8-13-74.

CROSS-REFERENCE TO RELATED APPLICATIONS

This invention is a continuation-in-part of our co-pending patent applications, assigned to the assignee of the present invention, Ser. No. 119,298 filed Feb. 26, 1971, issued as U.S. Pat. No. 3809977 and reissued as U.S. Pat. No. Re. 28,752 on Mar. 30, 1976, entitled ULTRASONIC KITS AND MOTOR SYSTEMS, and a continuation-in-part thereof, Ser. No. 209,971, filed Dec. 20, 1971, now U.S. Pat. No. 3924335 entitled ULTRASONIC DENTAL AND OTHER INSTRUMENT MEANS AND METHODS, which entire subject matter of the co-pending applications are incorporated herein by reference as if fully set forth herein.

BACKGROUND OF THE INVENTION

The field of the present invention resides in an electromechanical motor system in which the output applicator thereof is made to vibrate intermittently at an ultrasonic frequency, to produce bursts of ultrasonic mechanical vibrations repeated at a sonic frequency. The motor system thus produced is capable of producing effects characteristic of both ultrasonic and sonic vibratory devices.

Over the last decade a number of applications have been proposed and patented in which the introduction of ultrasonic mechanical vibrations has resulted in new and novel results. Towards this end the inventors of the present invention have pioneered in the development of ultrasonic motor-converter systems that could be manufactured and incorporated into home consumer products particularly where cost is a major consideration, as well as dental, medical, and industrial applications and uses. Towards this end the key consideration has been the development of a low cost converter-motor system that would permit the application of ultrasonic energy for use as in an ultrasonic home dental unit, ultrasonic shaving unit and ultrasonic hobby kit to name but a few. These and other uses are indicated in the referenced co-pending patent applications hereinafter referred to throughout the specification as the "applications" for convenience. A method and apparatus for the ultrasonic cleaning of teeth is disclosed in U.S. Pat. No. 3,375,820 which issued on Apr. 2, 1968 to Arthur Kuris and Lewis Balamuth while an ultrasonic method and apparatus for shaving is disclosed in U.S. Pat. No. 3,610,080, which issued on Oct. 5, 1971 to Arthur Kuris. The entire subject matter of said Letters Patent are incorporated herein by reference as if fully set forth herein.

The present invention provides for the first time a motor-converter system with a minimum number of electronic components that enables the manufacture, in the low power range of, for example, from 1 to 10 watts, of instrumentation for home and other use which combines the beneficial effects of vibrations in the ultrasonic range, defined herein to include vibrations in the frequency range of 10,000 Hz to 1,000,000 Hz, and in the low sonic frequency range, defined herein to include vibrations in the frequency range at 10 Hz to 1,000 Hz.

The inventors have discovered that there are many instances where it is desirable to produce a mechanical vibration which in effect is a series of high frequency vibration bursts separated by predetermined time intervals, the separating time intervals being large compared with the time intervals for a period of the high frequency vibration. Such mechanical vibration is capable of producing all the necessary high frequency effect essential to ultrasonic motor technology. However, the pulsing effect imparts to the motors' applicator a kind of "jiggling" or "buzzing" effect during use. Among other advantages to this specific result of the double frequency system herein described is found in the fact that the buzzing action of the applicator during use gives the user the psychological assurance that the system is doing its job.

This signalling of the presence of the operating condition of the device has been found to be necessary in consumer devices such as hobby kits, razors, toothbrushes and the like using ultrasonic vibrations for producing their respective operative effects. In the prior art hand held ultrasonic devices, the user feels no difference in sensation in the hand holding the device when the device is "on" and when the device is "off". To be sure, visual aids may be used, such as a small pilot light, or an auxiliary sonic device to help the user know the device is on, but such aids add expense to the device which is unnecessary and is eliminated by the simplicity of the solution to this problem disclosed herein. Further, not only is the foregoing problem solved by the arrangement in accordance with the invention, but further desirable operative effects are produced in at least some of the ultrasonic devices in question.

Thus, the arrangement in accordance with the invention produces the completely unexpected results of a low frequency macro-massage type action, simultaneously with the ultrasonic micro-massage and other uniquely ultrasonic effects (due to cavitation, etc.) normally expected from the ultrasonic devices in question. One of the most important consequences of the invention is the establishment of a uniquely new method for applying ultrasonic energy to tissues with the synergistic benefit of simultaneous micro-massage and macro-massage.

A further unexpected beneficial result of the method and devices in accordance with the invention is the dramatic improvements in the application of ultrasonic energy for periodontal procedures, primarily for use in the home. Ordinary toothbrushing uses bristles and tooth paste to keep tooth surfaces clean and hopefully, polished and bright, a condition usually characterized as "whiten". In addition, an attempt is made to clean out interproximal, gingival crest, or gumline areas, and other hard-to-get-at areas without too much success. Conventional dental teaching requires the toothbrusher to learn how to stroke the gingival-tooth boundaries so as to provide some gum stimulation. Electric-vibratory, i.e., 60 cycle per second, toothbrushes attempt to meet all the above goals with greater efficiency and with the aid of outside electrical energy to provide additional motion to the bristles during use. However, such electric-vibratory toothbrushes merely utilize the principles of conventional toothbrushing. Recently, dental science has recognized the need for the removal of plaque during home periodontal care as an assist to the professional care ordinarily supplied by the dentist. However, conventional home cleaning devices used in a conventional manner fail to remove plaque.

The inventors have discovered that the addition of high frequency mechanical vibration energy to such elements as bristles or stimulents or other applicators permits the removal of plaque, thereby extending the benefit in oral hygiene normally obtained from the dentist to safe self-administered procedures followed by the patient at home. As is usual with high frequency mechanical vibration devices the benefits are multivalued comprising the possibilities of micro-massage, fatigue destruction of calculus, interproximal cleaning due to cavitational energy in associated fluids being present, and the like.

The inventors have now found that the utilization of two frequencies in a vibratory system has produced unexpected beneficial effects, with each frequency performing its function such that the cummulative effect of the utilization of two frequencies exceeds the beneficial effect of either frequency working in its own frequency range. For example, with respect to the brushing or cleaning of teeth, it has been established that the high frequency energy is capable of moving plaque from the teeth with the low frequency introducing a macro-massage type action both on the gums and also cleaning teeth with respect to the effect that the low frequency range provides. Similar benefits are obtained in the field of shaving where the high frequency of vibratory energy plays its role as more particularly described in U.S. Pat. No. 3,610,080, and the low frequency component produces its own beneficial effect.

Aside from the ability for the first time to simultaneously utilize the beneficial results of two known frequency ranges in a single instrument, the arrangement and method in accordance with the invention produces results obtainable due to the combined effect of the two frequencies. Accordingly, the motor-converter system of the present invention may be utilized in such a manner that work may be performed on an object such that it may operate at an ultrasonic frequency and an audible frequency simultaneously with said ultrasonic vibrations. Since the current best ultrasonic motor art requires the vibration frequency of the motor to be at or near one of the natural vibration resonance frequencies of the motor, the current invention may use an automatic frequency control/feedback circuit which guarantees a selection of the desired aforementioned resonant mode.

SUMMARY OF THE INVENTION

Generally speaking, in accordance with the invention, a method for performing work on a object is provided including the steps of positioning an applicator capable of physical vibration at an ultrasonic frequency adjacent the object, inducing vibrations in said applicator at a frequency in the ultrasonic range and modulating the ultrasonic frequency of said applicator at a sonic frequency so as to produce spaced bursts of ultrasonic vibration in said applicator. To remove foreign matter including plaque and other surface deposits from teeth, the method in accordance with the invention would consist of the steps of positioning adjacent the teeth to be cleaned a plastic surface capable of supporting and transmitting ultrasonic vibrations, vibrating said surface in spaced bursts of vibrations in the ultrasonic frequency range, said bursts being repeated at a sonic frequency, and moving said vibrating surface relative to said teeth so that it engages and removes the deposits therefrom. Said surface is in the form of a plurality of individual bristle elements such that the elements assume positions in which they are randomly divided between actual contact with and displacement from the surface of the teeth. A fluid film may be provided at the teeth surfaces.

Shaving hair by the method in accordance with the invention includes the step of generating ultrasonic vibrations in the cutting edge of a blade coupled to a hand-held ultrasonic motor, applying bursts of ultrasonic vibrations at said cutting edge, said bursts being repeated at a sonic rate, and engaging said cutting edge adjacent the hair to be shaved in a relative moving relationship.

The systems in accordance with the invention include vibratory means capable of physical vibration at an ultrasonic rate and driving circuit means electrically coupled to said vibratory means for applying a driving signal to said vibratory means for sustaining the vibration thereof, said driving signal consisting of ultrasonic portions repeated at an audio rate to produce bursts of ultrasonic vibrations in said vibratory means repeated at said audio rate. Said vibratory means may include a transmission member having an output and at which said vibrations are produced and transducer means physically engaging said transmission member and electrically coupled to said driving circuit means. Said vibratory means may define an ultrasonic motor mounted in an ultrasonic instrument means adapted to be hand held by the user thereof. Interchangeable means may be provided adapted to be secured to the front end of the ultrasonic instrument means to permit a variety of applications of ultrasonic mechanical vibrations to a selected object for various results. Said interchangeable means may be in the form of a razor, a toothbrush or the like. The driving circuit means may include oscillator circuit means for producing a signal at said ultrasonic frequency and modulating circuit means coupled to said oscillator circuit means for modulating said ultrasonic frequency signal at a sonic frequency to produce said driving signal. Said ultrasonic motor may be capable of vibration at a plurality of ultrasonic frequencies including a desired frequency, and said driving circuit means may include tuned circuit means tuned to said desired frequency for controlling the frequency of said driving signal and means for applying a detected signal representative of the frequencies of vibration of said ultrasonic motor to said tuned circuit means, the tuned circuit means responding to the desired frequency portion of the detected signal to cause said driving circuit means to produce a driving signal of the desired frequency.

OBJECTS OF THE INVENTION

A primary object of the present invention is to provide a variety of ultrasonic converter system having both ultrasonic and sonic frequency characteristics adaptable for both consumer and commercial use.

Another object of the present invention is to provide an ultrasonic system wherein bursts of ultrasonic vibrations are produced at an applicator, said bursts being repeated at an sonic frequency.

Still another object of the invention is to provide an ultrasonic motor-converter system incorporating interchangeable accessories permitting a wide variety of uses.

A further object of the invention is to provide a new and novel ultrasonic motor-converter system.

Still another object of the invention is to provide a new and novel dual frequency driving circuit for ultrasonic devices.

Another object of the present invention is to provide a new and novel method of applying ultrasonic mechanical vibrations.

Still another object of the present invention is to provide improved methods and apparatus for performing oral hygienic procedures with ultrasonic energy.

A further object of the present invention is to provide novel and improved cleaning techniques for personal oral hygienic care which enables the user to control and obtain significantly better cleaning of teeth.

Still a further object is to provide new and novel methods and apparatus which are embodied in a device that is completely safe for use by adults and children in the home on a regular basis.

Another object of the present invention is to provide new and novel methods and apparatus for regular personal oral hygienic care which provides excellent cleaning results in the hard to reach interproximal and gumline areas in general, and simultaneous gum stimulation.

Still another object of the present invention is to provide improved cleaning techniques for the removal of plaque, tartar, calculus, stubborn stains and interproximal soft debris.

Another object is to provide an ultrasonic oral hygene device providing a sensual indication of its operation during use.

A further object of the present invention is to provide methods and apparatus employing ultrasonic and sonic energy simultaneously for shaving of skin and which is completely safe for use in the home.

Still a further object of the present invention is to provide novel forms of shaving apparatus and improved shaving techniques employing sonic and ultrasonic energy in which the frictional resistance to movement of the shaving instrument over the skin is substantially reduced.

Another object of the present invention is to provide a novel and improved shaving technique and apparatus employing sonic and ultrasonic energy which may be employed with or without a shaving cream.

Still another object of the present invention is to provide an ultrasonic shaving apparatus providing a sensual indication of its operation during use.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

Although the characteristics features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 3 is a view of an electrical circuit of the invention to obtain the dual frequency;

FIG. 5 is a front view of the ultrasonic home oral unit in accordance with the present invention;

FIG. 6 is an end view of the ultrasonic home oral unit in accordance with the present invention;

FIG. 7 is a side view in cross-section of the ultrasonic home oral unit in accordance with the present invention;

FIG. 8 is an enlarged sectional view of a portion of the unit in FIG. 7;

FIG. 9 is an enlarged sectional view of a portion of the unit in FIG. 7;

FIG. 14 is a view of an electrical circuit similar to that discussed in FIG. 3 but of another form of the invention;

DESCRIPTION OF THE PREFERRED EMBODIMENTS

Figure 11:
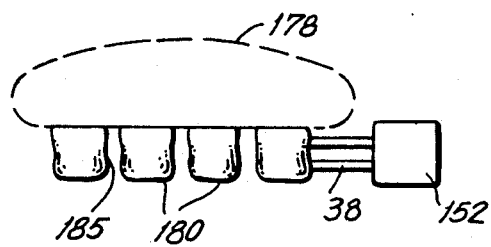
FIGS. 10–13 illustrate the cleaning system of the present invention in relation to a set of human teeth and are helpful in explaining the process of the instant invention.

Referring to the drawings in detail, and initially to FIGS. 1, 2a, 2b and 2c, the theory relating to the present invention in which two frequency components are employed in a mechanically vibrating ultrasonic motor will be described. In the art, ultrasonic motor-converter systems are generally adapted to produce mechanical vibrations in the form of a continuous, simple harmonic vibration of constant amplitude, as depicted in FIG. 11, waveform 10 having a constant vibration amplitude 11 and a period of oscillation $\tau_2$. These ultrasonic vibrations generally lie in the frequency range including 10,000 Hz to 1,000,000 Hz. One characteristic of such ultrasonic vibrations is that a solid surface vibrating at an ultrasonic frequency is actually felt in a different way than when the surface is not vibrating. During ultrasonic vibration, friction between the solid vibrating surface and an object placed in engagement therewith is drastically reduced, in large measure due to the acceleration of the vibrations, which in the case of ultrasonic vibrations, is at least 1,000 g.

Figure 1:
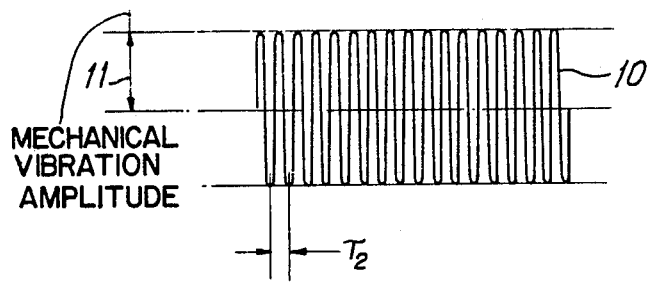
FIG. 1 is a diagrammatic view of the waves of the ultrasonic frequency pattern.
Figure 2A:
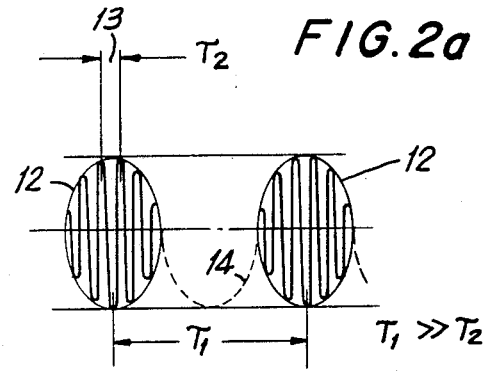
FIGS. 2a and 2b are diagrammatic views to illustrate the theory of the present invention in which two frequency components are employed.

The inventors have now discovered that in many instances it is desirable to produce a mechanical vibration of the type shown in FIG. 2a, which consists of a series of high frequency vibration bursts 12 separated by equal time intervals 14, said separating time intervals being large compared with the time interval 13 representing the period of the high frequency vibration ($\tau_2$). As is apparent from an examination of FIG. 2a, the bursts of high frequency vibration are defined by half sine wave envelopes, the width of each envelope being equal to time interval 14. Bursts of high frequency vibration 12 are repeated at a sonic or low frequency having a period $\tau_1$. For an ordinary 110 volt 60 cycle A.C. source of voltage, $\tau_1$ would correspond to 1/60 sec. If the natural resonant frequency of the high frequency vibration is 30,000 Hz, $\tau_2$ is 1/30,000 sec. Expressed in microseconds, $\tau_2$ would equal 33.4 $\mu$sec. and $\tau_1$ would equal 16,000 $\mu$sec. The frequency of repetition of the bursts of high frequency vibrations lies in the sonic range, and more particularly between 10 Hz and 1,000 Hz. In the example given, each burst of high frequency vibration would include as many as 5,000 complete reciprocations.

Figure 2B:
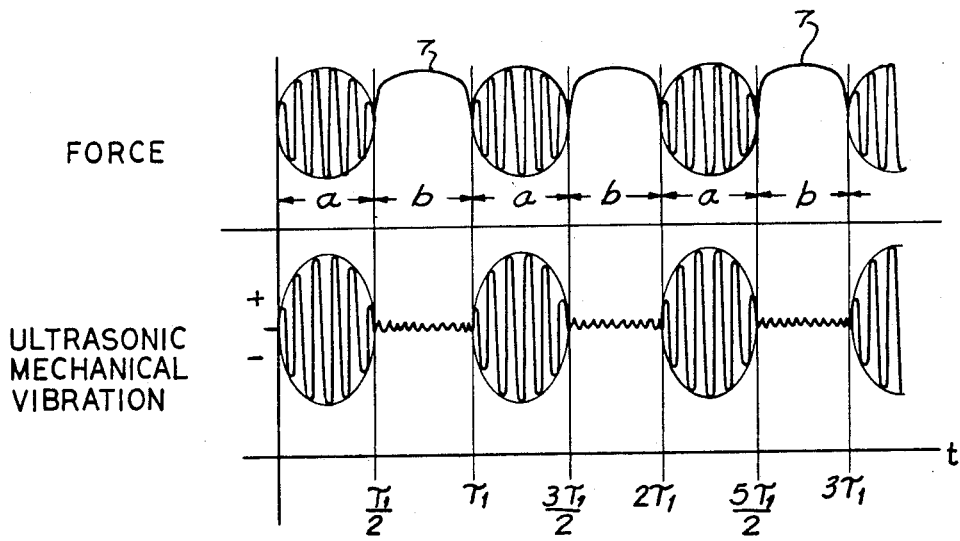
Figure 2C:
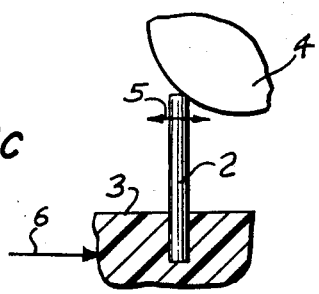
FIG. 2c is a fragmentary view of an element vibrated in accordance with the invention and its interaction with a surface.

It has been found that when an electro-mechanical transducer or ultrasonic motor is vibrated as indicated in FIG. 2a by bursts or packets or ultrasonic vibrations, the user experiences a definete physical sensation when an applicator mounted on said transducer or motor is engaged against a surface. This sensation, described as buzzing or jiggling permits the user to distinguish between the conditions during which the applicator is on and when said applicator is off. The drastic reduction in friction caused by ultrasonic vibrations prevents the experience of any such physical sensation when a prior art ultrasonic applicator is used. The buzzing or jiggling appears to occur at the sonic or low frequency and is believed to be caused by the difference in the frictional forces between the applicator and the surface engaged by the applicator during the bursts of ultrasonic vibration and in the interval between such bursts. Specifically, during ultrasonic vibrations, friction between the ultrasonic applicator and the surface is drastically reduced as compared with the friction during the interval between said bursts. The resulting, alternating "slip-stick" effect between the applicator and surface is believed to cause said buzzing or jiggling. The forces at work when an applicator is vibrated in accordance with the invention as depicted in FIG. 2a is indicated by a consideration of FIG. 2b and 2c. In FIG. 2b, the lower waveform represents the actual ultrasonic mechanical vibration of an applicator, such as toothbrush bristle 2 mounted on a vibrating head 3 when engaging against a tooth or gingival surface 4. The ultrasonic vibrations within each burst is in the direction represented by double-headed arrow 5.

Each burst of ultrasonic mechanical vibration lasts for a half period ($\tau_1/2$)$_3$ of the sonic modulation frequency. In an actual device, during the interval b between bursts the device would be vibrating at an ultrasonic frequency, but at a very low amplitude. During interval a, the frictional force of the bristle 2 against tooth 4 is reduced resulting in a slipping action. However, at the same time, during each individual high frequency reciprocation there is an impulsive force represented in the upper waveform of FIG. 2b. This impulsive force pulls on the surrounding liquid (saliva, mouthwash, dentifrice, or whatever fluid is present,) and cavitation results. Each returning pushing force in the liquid causes the cavities to collapse with consequent production of shock waves. All of this action is rapidly repeated during intervals a. The dynamics of the force present in interval a is extremely complex, the representation in FIG. 2b being intended as schematic and suggestive of the forces present. During intervals b, we have a relative period of rest, insofar as high frequency vibration is concerned. The reduction in frequency is dependent on the presence of relative high amplitude ultrasonic vibrations, the low amplitude vibrations present during interval b not being sufficient to reduce the frequency, and a sudden rise in frictional force occurs. This sudden rise in frictional force is related to the ordinary brushing force represented by arrow 6 in FIG. 2c which would be present if the brush were used with no high frequency vibration at all, and results in the normal displacement of the brush by the user. This sudden rise in brushing force occurs as the high frequency vibration force disappears and will continue during the interval b, which can be characterized as a "stick" interval. Thus, due to the stick-slip effect of the alternating sonic modulation of the high frequency vibration, a succession of force peaks 7 is produced. In effect, this is somewhat like the introduction of a sonic "tapping" of the tooth gingival structure, the tapping frequency corresponding exactly to the sonic modulation frequency ($1/\tau_1$). Thus, the method and apparatus in accordance with the invention subject the surface engaged by the ultrasonic applicator, and in this case, the teeth and gums to a complex series of dynamic actions incorporating both sonic and ultrasonic frequencies of energy. During each interval a, an ultrasonic quanta of energy is applied, while during each interval b, a peak of energy representative of the brushing force is applied. Since the brushing force peaks and the ultrasonic quantas of energy alternate at a sonic rate, it may be said that the method and apparatus in accordance with the invention produces successive time periods of high frequency and low frequency effects. As used herein, the term "simultaneously", as applied to these effects, merely refers to the fact that during a fraction of a second, both effects are repeated many times. Thus, for a 100 Hz sonic modulation frequency, there would be in 1/10 of a second, thousands of reciprocal high frequency actions and 10 low frequency actions. It is this unique set of actions which produces the synergistic results, one of which is the rapid and complete removal of plaque from teeth including the interproximal regions, together with macro- and micro-massage of the gingival tissues. A further effect is the buzzing or jiggling sensation experienced by the user. In addition, all of the necessary high frequency effects essential to ultrasonic motor technology are produced during the bursts of high frequency vibration.

Referring now to FIGS. 3–9, an embodiment 20 of the arrangement in accordance with the invention is depicted including an instrument means 25 in combination with driving circuit means 30 that work together in unison to perform a variety of applications, as for example that of toothbrushing. The embodiment 20, for example, is designed to permit daily use by a person in the home of a toothbrush, the bristles of which are ultrasonically vibrated in bursts repeated at a sonic frequency. In this embodiment, the sonic frequency is 60 Hz, and while the toothbrush is effective for the removal of plaque, which is generally recognized as a principal souce of calculus formation and possible subsequent loss of teeth due to peridontal disease, and stimulation of the gingiva, especially at the tooth-gingiva junction regions, the total power level introduced into bristles 38 is considerably less than 1 watt. It is noted that the ultrasonic vibration of bristles 38 is invisible to the naked eye.

Instrument means 25 includes handle means 26 adapted to be hand held by the user in a conventional manner, and also has a detachable applicator means or assembly 35 containing a bristle cluster or stimulent 38 to be ultrasonically vibrated. Extending from one end of instrument 25 is supply means 32 in the form of and electrical cable for transmitting power, in the form of a driving signal from driving circuit means 30 to instrument means 25. Driving circuit means 30 is mounted within a cabinet 130, and power for said driving circuit means may be obtained from a standard electrical outlet (a 60 Hz A.C. source) by means of electrical cord 134 terminating in plug 132. A switching means 40 is mounted on cabinet 130 consisting of a switch 42 connected in the power line for the selective energization of the ultrasonic transducer or motor 45 contained within the housing defining handle means f26. Supply means 32 consists of flexible conduit 52, through which leads 44, 46, 48 and 100 extend. Line 44 is a separate grounded cable connected to the ground of the electrical outlet plug. The ultrasonic mechanical vibrations of bristles 38 as indicated by arrow 41.

Driving circuit means 30 is preferably of the solid state type and may have a power rating of as small as 1 to 4 watts, and is generally within the range of 1 to 10 watts. The actual mechanical power delivered to the bristles and subsequently to the gingiva and teeth of the user is variable depending on the pressure and movement of the bristles by the hand of the user. In the case, the power under maximum conditions is but a minute fraction of the power delivered to the motor 45.

Essentially, ultrasonic motor 45 as hereinafter described is designed, depending upon the use thereof, to accept a variety of applicator means 35 and the magnitude of ultrasonic mechanical vibrations to be imparted thereto may be selected by proper motor design. The motor 45 includes a transmission member 50 which has a rear section 54 and front section 56, which may of circular cross-section, with a counterbore or seat 58 extending from its rear face 60 to a bottom surface 62. Mounting means 65 is provided and includes a radial seat 66 adapted to contain therein means as in the form of an O-ring 68.

The transmission member 50 has a contoured-radius connecting portion 70 connecting together the front section 56 and the rear section 54 of the transmission member 50, which sections may both be of circular cross-sectional area. The front section 56 extends out beyond the front end 74 of the tubular housing 72 a sufficient distance. The motor mounting means, although illustrated to be in the form of an O-ring 68, may take other forms and shapes as desired.

The ultrasonic motor 45 in conjunction with the applicator means 35 is longitudinally dimensioned so as to have lengths which are generally whole multiples of half-wavelengths of the compressional waves established therein at the resonant frequency of the combined longitudinal length of the components so that longitudinal loops or other components of motion occur at the end 78 of the applicator means 35. Thus, the optimum amplitude of longitudinal vibration and hyperaccelerations of transmission is achieved, and such amplitude is determined by the relationship of the masses of the rear section 54 and the front section 56 which may be made effective to either magnify or reduce the amplitude of the vibrations received from the transducer crystal. In the usual case, transmission member 50 serves as an amplifier. The front section 56 may be permanently attached to applicator means 35, or the front section 56, or part thereof, may be provided with a threaded stud 160 adapted to be screwed into a tapped hole 162 in the end of the transmission member 50 for effecting rigid connection of the applicator means 35.

A piezoelectric element such as crystal 80 is mounted within the cavity means 58 of the rear section 54 and it may be of tubular shape and in the embodiment shown comprises a lead zirconate-lead titanate ceramic crystal which is formed so as to be capable of ultrasonic vibrational activity in its longitudinal direction when activated by high frequency electrical impulses delivered to it as will be desired.

The crystal 80 is mechanically joined by a hardening cement 82 of, for example, the epoxy type which, upon setting, becomes rigid and provides a solid direct mechanical coupling between the front end portion 84 of crystal 80 and rear section 54 of transmission member 50 so that ultrasonic longitudinal vibrations of the latter are directly transmitted to said rear section 54 to form a compound resonator. As shown in FIG. 9 the rear section 54 has a skirt portion 86 which extends downwardly over the front end 84 of crystal 80 and a recessed portion 58 is provided to receive the epoxy cement 82 to circumferentially surround the front end of crystal 80.

Crystal 80 is provided with an electrically conductive silver coating 92 on the inner wall 88 thereof of approximately 0.0015 inch in thickness. Conductive coating 92 may extend along the entire length of said inner wall 88 or within ¼ inch of the end of said inner wall. A similar silver coating is formed on outer wall 90 of crystal 80, the latter conductive coating being in two sections, a main section 93 extending along all of surface 90 of crystal 80 except for the end regions thereof, and an annular portion 96 on the rear portion of outer wall 90, separated from main portion 93 by a gap 98. Such coatings may be applied by electro-deposition or any other conventional process. Driving circuit means 30 is electrically connected with ultrasonic motor 45 by means of leads 44, 46, 48 and 100. Lead 44 is soldered to end wall 62 of rear section 54 of transmission member 50 to specifically ground said transmission member. Lead 48 is soldered to conductive coating 92 while lead 46 is soldered to conductive coating 93, conductive coatings 92 and 93 cooperating to apply the driving signal to crystal 80. Finally, lead 100 is soldered to the annular conductive coating 96, which, together with a portion of conductive coating 92 defines a oscillation detector means.

A driving signal oscillating at the proper frequency delivered along leads 46 and 48 to conductive coatings 92 and 93 from driving circuit means 30 will produce the desired piezo-electric effect and ultrasonic longitudinal vibration of crystal 80 and applicator means 35. The ultrasonic vibrations are created in crystal 80 and transmitted directly to applicator means 35, so that when bristles 38 are applied to a tooth or other surface to be cleaned, the vibrations serve to perform the desired cleaning function. The vibrations are created in crystal 80 by the expansion and contraction thereof in the longitudinal direction when excited by a high frequency electrical driving signal. The crystal and transmission member 50 are specifically designed to be resonant at a particular frequency, for dental applications, preferably about 35,000 Hz. In fact, the ultrasonic motor depicted does not have a single natural resonant frequency mode of operation, but rather, has a whole spectrum of possible modes which include subharmonics and harmonics of the design operating mode frequency. It is preferable to design the ultrasonic motor so that it oscillates at a frequency which will produce the highest Q. The Q at idle is selected to fall within the strain limits of endurance of the motor. The motor is further designed for peak efficiency under load, i.e., when bristles 38 are engaged against the tooth and gingival surfaces of the user. If the loaded Q drops significantly below the Q of the other resonant modes of vibration of the ultrasonic motor, then, under load, the motor will "hop out of tune" and vibrate at this other frequency. If this occurs, the device would become ineffective because the motor is not designed for efficient operation in the new frequency mode. This problem is solved by the provision of the detecting electrodes defined by conductive coating 96 and the overlapping portion of conductive coating 92 and by the design of the driving circuit means 30 as will be more particularly described below.

Crystal 80 can be electrically energized, if desired, to have vibratory components in other than the longitudinal direction to provide various mechanical effects. This would be accomplished by changing the excitation frequency. In addition, the location of application of the voltage to the crystal can be utilized to produce different effects. For example, by applying the voltage across opposite ends of the crystal, a torsional effect is produced.

When driving circuit 30 is energized, as by closing power supply switch 42, the sudden surge of current therefrom will drive crystal 80 into a vibratory mode of operation. The vibrations of crystal 80 will in turn induce vibrations in the detector electrodes so that a signal representative of the frequencies of vibration of the ultrasonic motor 45 is transmitted back along line 100 to driving circuit means 30. As shown in FIG. 3, said circuit includes a variable inductor 120 and capacitor 106 connected in series with line 100 to receive the detected feedback signals. Said inductor and capacitor define a tuned circuit which is turned to the design frequency of motor 45 so that, only the portion of the detected signal at the desired frequency is passed by said tuned circuit. In effect, the tuned circuit serves as a filter, the filtered signal of the desired frequency being applied to the base 104 of transistor 102 which serves to amplify the detected signal. The emitter 116 of transistor 102 is connected through resistor 118 to ground while the collector 114 is connected through primary winding 110 of transformer 112 to line 124, which in turn is connected to a power supply. This power supply consists of the normal A.C. 60 Hz power supply, which is connected through lines 34 and 36, line 36 being grounded. Line 34 connected through switch 40 to diode 125 which serves as a half-wave rectifier of the A.C. signal. Lines 34, 36 are coupled by a capacitor 122 which provides D.C. isolation and some minor smoothing. The resultant, essentially half-wave signal is applied to line 124 to modulate the ultrasonic frequency electrical signal applied to the base 104 of the transistor. The resulting half-wave bursts of ultrasonic oscillation, said bursts being repeated at a 60 Hz frequency, are applied to lines 46 and 48 through transformer 112 for driving ultrasonic motor 45.

Driving circuit 30 thus serves to sustain the ultrasonic vibrations of motor 45 within each burst of vibrations at the desired frequency through the mechanism of the detector electrodes and the tuned circuit defined by inductor 120 and capacitor 106. Further, by modulating the ultrasonic frequency oscillating signal by a half-wave rectified 60 Hz signal, the desired bursts of ultrasonic vibration are produced. While the embodiment of FIG. 3 depicts a driving circuit having an A.C. power line as a power source, the arrangement in accordance with the invention could also be driven by a battery, in which case a suitable sonic frequency oscillator circuit would be provided for producing half-wave signal of a sonic frequency for modulating the ultrasonic frequency singal applied to the base of transistor 104.

Figure 4:
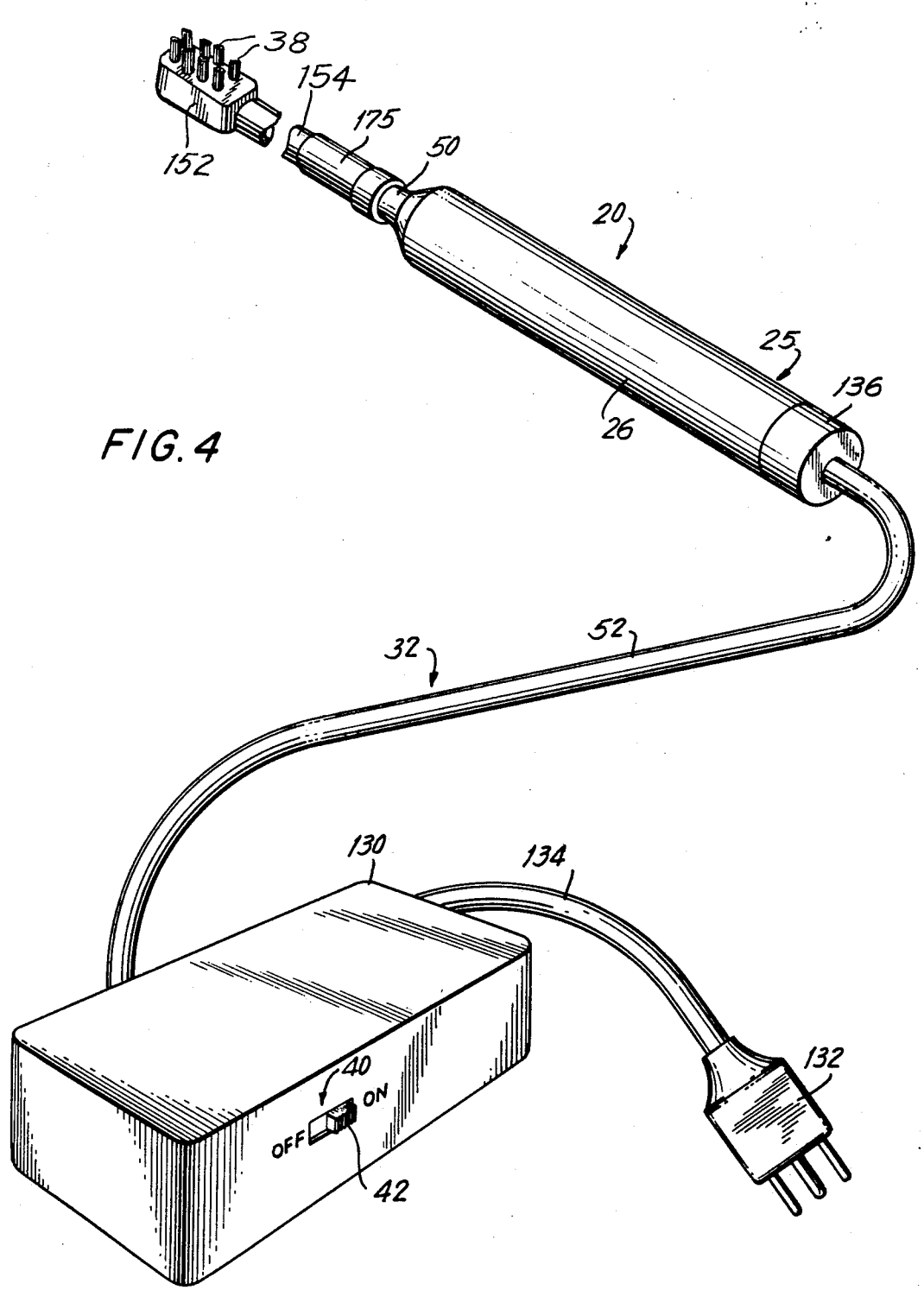
FIG. 4 is a perspective view of an ultrasonic home oral unit in accordance with the present invention.

It will appreciated by one skilled in the art, that the entire driving circuit means can be formed from about eight components, a very small number permitting the production of very compact and light weight driving circuits. The precise values of the respective components depends on the power output of the device. But, as illustrated in FIG. 4, the driving circuit may be mounted in a relatively small housing 130. The components may easily be contained in a rectangular area having the dimensions 1 ½ × 2 × 1 ½ inch. Switching means 40 mounted on said cabinet permits the user to selectively turn the toothbrush on or off as desired. Not only does the foregoing construction reduce size, it substantially reduces the cost thereof to the point where a consumer product becomes feasible. As shown particularly in FIG. 7, housing 72 may be injection molded or formed in an acceptable manner and includes a rear section plug 136 that fits in telescopic relation with the housing 72 and having an aperture 138 extending axially therethrough for receiving flexible conduit 52 of supply means 32 to retain said flexible conduit in fixed position relative to plug 136. A clip 140 is positioned around conduit 52 to retain the latter such that the user cannot apply any tension on leads 44, 46, 48 or 100 during use of the instrument. A pin 142 is seen to extend through the wall of handle housing 72 and into a pocket in plug 136 so as to retain the latter in fixed position. Various means may be used for this purpose. To retain the motor 45 in fixed position relative to the housing 72, retaining means 145 may be employed. As seen particularly in FIG. 9 the retaining means may include a dowel or pin 146 that extends transversely through the housing wall 144 and into a pocket or seat 148 contained within the rear section 54 of the transmission member 50 so that the latter remains in fixed position relative to the housing 72 when the user either initially secures the applicator means 35 to the instrument means 25 or removes it therefrom. Obviously, other forms of retaining means may be employed to maintain the coupled relationship so that rotational movement is prohibited between the transmission means 50 and the housing 72.

As seen particularly in FIG. 9, the front end 74 of the housing 72 may have a lip 150 that blends with the connecting portion 70 of the transmission member 50. Mounting means 65, which also includes O-ring 68, also acts to seal the inner chamber of the handle means 26 from any fluid that might try to seep into the instrument during use by the user.

Applicator means 35 may take various forms, shapes and configurations, so long as it is designed so that the complete system will operate in tune whether the instrument is out of engagement with any surface, such as in the air, or in engagement with a surface which may be the oral cavity of the user or may be the face of the user where the applicator means is a shaving device. The apparatus in accordance with the invention is particularly adapted to maintain the combined ultrasonic motor-applicator means vibrating at the desired frequency at various load conditions, and to modulate such vibrations so as to produce bursts of ultrasonic vibrations. It is the ability to obtain and maintain this vibratory condition with the combination of electronic circuitry and ultrasonic motor which is a particular feature of the present invention.

The applicator means 35 in this embodiment of the invention is illustrated as an ultrasonic toothbrush which is more fully disclosed and described in a simultaneously filed co-pending patent application assigned to the assignee of the present invention and entitled "Ultrasonic Toothbrush Applicator," Ser. No. 318428 now Pat. No. 3828770 issued on Aug. 13, 1974 which may be referred to for a more detail discussion of a form of brush applicator that may be used in conjunction with the present invention and reference thereto may be had for information, but by no means limitation thereto. Essentially, the brush applicator includes a body portion 152 having a plurality of bristle clusters 38 extending therefrom at substantially right angles thereto and terminating prior to the end face 78. The body portion 152 merges with a neck portion 154 and terminates at an end face 156. Coupling means 160 is provided for proper transmission of the ultrasonic and sonic vibratory energy from the end of front section 56 of transmission member 50. Said transmission member has an axially extending tapped hole 162 which receives therein threaded stud 164 which merges with a flange portion 165, which in turn has a threaded portion 166 extending from the opposite end thereof in axial alignment with the threaded stud 164. The threaded portion 166 may be firmly secured within complimentary threads 168 contained within the body portion 154, a bonding agent 170 being provided therebetween to help couple the energy between threaded portion 166 and the body portion 154. If coupling means 160 is injection molded in combination with the plastic applicator means 35, then the bonding agent can be dispensed with since an intimate coupling between the two threads is obtained and sufficient energy transmission is realized to properly transmit energy to vibrate the bristle clusters 38 which in turn produce the vibrating motion in accordance with the invention. The flange portion 165 may be of a cross-sectional area such as hexogonal to permit ready grasp by either mechanical means such as a wrench or by the hands of the user to assure that the bottom face 172 is in intimate contact with the output end or front face 61 of the output section. An axial bore 174 may be provided, if required, as to control the total cross-sectional area of the body portion 154 so as to obtain the proper transmission of vibratory energy to the head portion 152 and in turn the bristle clusters 38.

To provide a protection for flange portion 165 and the body portion 154, a sleeve 175 may be shrink fitted as seen in FIG. 9 to properly encompass the material which it covers. The sleeve 175 may be of a plastic material and may also act as insulation.

Turning now to FIGS. 10–13, there is illustrated a portion of the dental cleaning procedure in accordance with the invention in operative position in the oral cavity 178 against the teeth 180.

The brush construction may be that which resembles closely an ordinary manually actuated toothbrush or designed more particularly as set forth in the co-pending patent application entitled "Ultrasonic Toothbrush Applicator" hereinabove referred. In accordance with the invention, the brush bristles 38 of the applicator means 35 is positioned against the teeth 180 in the usual manner during the brushing operation. That is, the bristle clusters 38 are inserted in the mouth and positioned adjacent the tooth surfaces 183 with a relatively light pressure. The bristle clusters 38 may be moved manually to pass the brush portion across all of the tooth surfaces, the bristles 38 randomly assume positions in contact with and displaced from tooth surfaces. Since in the case of manual brushing, the bristle elements 38 rarely assume positions such that they extend deeply into the interproximal areas 185 the present brush is designed to approximate the curvature thereof.

In this manner the action between the sonic motion and ultrasonic motion is believed to result in a combination effect such that the beneficial features of each frequency is simultaneously obtained.

Figure 10:
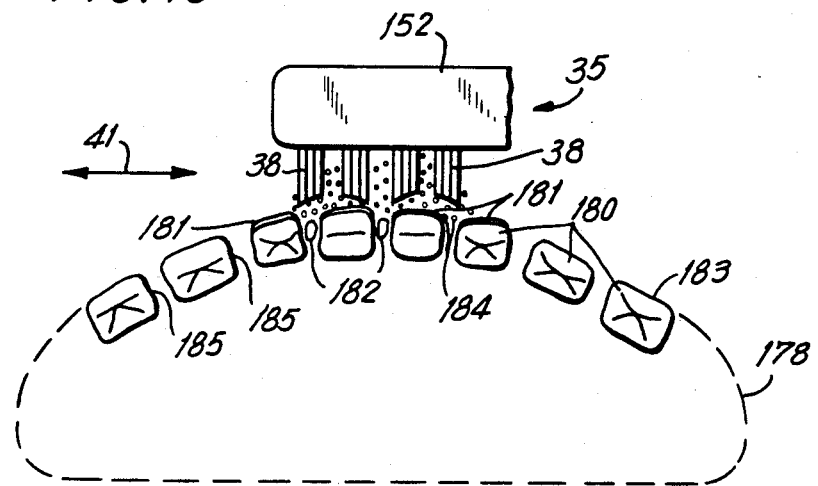

Accordingly, the removing of plaque 181 on the tooth surface 183 and foreign deposits 182 are obtainable with the present invention. In FIG. 10 plaque is shown as a coating that has adhered to the surfaces of the teeth 180. Plaque, a soft gelatinous substance produced in the mouth by the action of salivary and subgingival bacteria, hardens into calculus in a period of from two to twelve days, and is believed to be a significant factor in causing periodental disease.

In use, the bristle clusters 38 are vibrated in accordance with the invention so as to introduce a micromotion and a macro-motion as described above. When bristle elements 38 are lightly engaged against the teeth surface 183 and a relative moving relationship is maintained there is generated sufficient action to removed the plaque 181 and interproximal deposits 182. This action is generally obtained by providing a fluid film as illustrated by the particles 184 which may be in the form of a dentifrice having certain characteristics such as mild abrasive characteristics, water or simply that of saliva. The ultrasonic motion at the bristle elements 38 is of sufficient amplitude of vibration to also produce a cavitational action in the fluid film 184.

In addition, the present invention permits stimulation of the gingival tissue by macro-massage and micro-massage which has been found beneficial for dental health, said massage also resulting in more blood circulation than is obtained by conventional brushing techniques. In addition, the stick-slip effect produces a sonic audible vibration due to the tapping of the bristles against the teeth which helps the user psychologically by communicating to him the fact that the instrument is working.

The angular positioning of bristle clusters 38 with respect to the applicator means 35 is substantially normal to the longitudinal mode of vibration, but this relation can be varied. Further, the ultrasonic vibration applied to applicator means 35 may be other than a pure longitudinal vibration. Thus, a radial mode of motion may be applied to said applicator means. Furthermore, the length and stiffness of the various bristles may be varied within the confines of the present invention and beneficial results may still be obtained.

Figure 13:
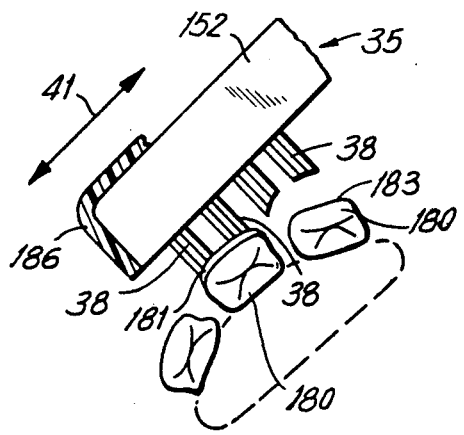
Figure 12:
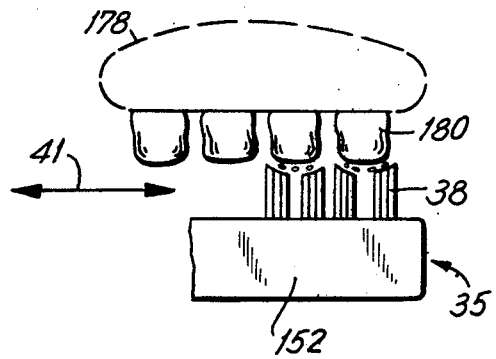

The bristle elements 38, as seen particularly in FIG. 13, may have a contoured surface configuration that lead themselves to conform to the contour of teeth 180 such that the bristle elements form a surface consisting of a multiple number of pointed members interproximately of the teeth during the brushing thereof which produces peak acceleration in the bristle elements.

One aspect of the present invention is to provide an insulated coating 186 that may surround the toothbrush head 152 to improve efficiency in that the coating 186 may be of a material which prevents transmission of high frequency vibratory energy into liquid, teeth or gums. This is readily accomplished, for example, with a closed cell rubber sheet 186. The closed cell layer 186 presents to the vibrating surface an acoustic impedance equivalent to that of an air film. The acoustic impedance of air is so mismatched i.e., so much smaller than the acoustic impedance of the brush head plastic 152 that all ultrasonic energy waves arriving at the brush head-closed cell interface will be almost totally reflected back into the plastic thereby making more energy available to the bristle clusters 38 to do their work.

Figure 18:
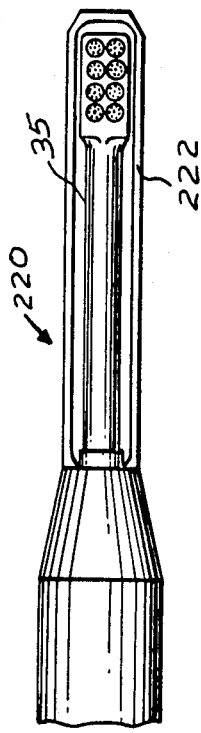
FIG. 18 is a fragmentary side elevational view of the head portion of a further embodiment of the home oral unit in accordance with the present invention.
Figure 19:
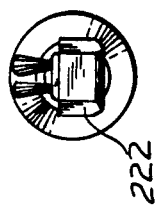
FIG. 19 is an end view of the home oral unit in FIG. 18.
Figure 20:
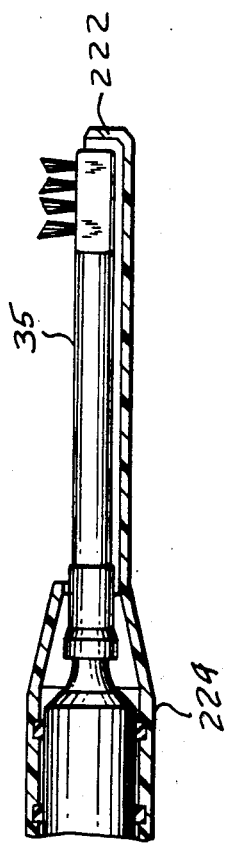
FIG. 20 is a further side elevational view of the home oral unit in FIG. 18 with the housing in cross-section.

Referring to FIGS. 18-20, the instrument 220 depicted differs from the instrument depicted in FIG. 3, in that a cowling or hood 222 extends about the sides, rear and end of applicator means 35 so as to prevent engagement of said applicator means with the cheak or jaw of the user. Cowling 222 is formed integral with housing 224 as more particularly shown in FIG. 20.

Referring now to FIG. 14, the system 20a depicted is essentially identical with the system of FIG. 3, except that driving circuit 30a is provided with a resistor 120a in place of variable inductor 120. This construction assumes that the ultrasonic motor 45 is designed so as to be stable in its frequency of operation when subjected to normal loads experienced in toothbrushing, so that the tuned circuit arrangement of FIG. 3 is not required. In all other respects, the arrangement of FIG. 14 is identical to the arrangement of FIG. 3.

Figure 15:
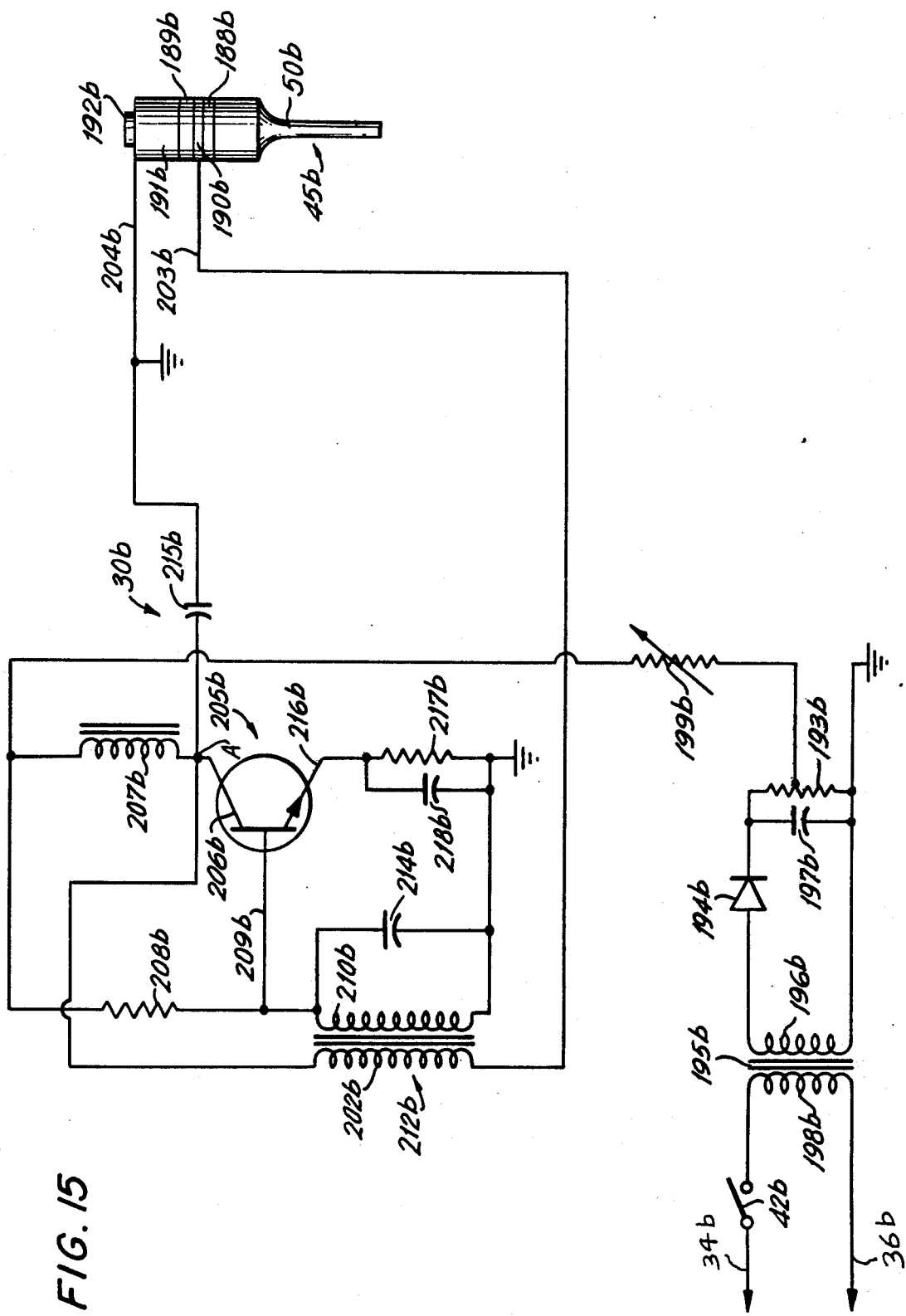
FIG. 15 is a view of another form of electrical circuit in accordance with the invention.

Referring now to FIG. 15, a further type of driving circuit and ultrasonic motor combination is depicted. The ultrasonic motor is provided with a pair of crystals 188b and 189b having an electrode 190 therebetween. Motor 45b further includes a rear portion 190b and locking means in the form of a nut 192b for holding rear portion 191b and locking means in the form of a nut 192b for holding rear portion 191b, crystals 188b and 189b and electrode 190b in compressed engagement with transmission member 50b. Driving circuit 30b is coupled to motor 45b by lines 204b and line 203b. Line 203b is electrically connected to electrode 190b while line 204b is grounded and connected to rear portion 190b. This embodiment does not have a crystal detector arrangement for sustaining the motor at the desired frequency. Rather, the frequencies of oscillation of motor 45b are reflected back through lines 204b and 203b to driving circuit 30b where they are detected for the purpose of controlling the frequency of the driving signal applied to said motor for sustaining the vibrations thereof. Driving circuit 30b includes a transistor 205b. The emitter 216b of said transistor is connected through resistor 217b to ground. Resistor 217b is shunted by a capacitor 218b. The collector 206b of said transistor is connected through choke 207b to variable resistor 199b, which in turn is connected to the power source. The junction between collector 206b and choke 207b is connected through capacitor 215b to line 204b and is connected to the primary winding 202b of transformer 212b, the other end of said primary winding being connected to line 203b. The secondary of transformer 212b is connected in parallel with a capacitor 214b to define a tuned tank circuit. Said parallel-connected circuit is connected between ground and the base 209b of the transistor. Said base is also connected through resistor 208b to resistor 199, for biasing said base.

The power supply is connected to the normal A.C. 60 Hz source through lines 34b and 36b, and in turn is applied to the primary winding 198b of transformer 195b. The secondary winding 196b of said transformer is coupled between ground and a diode 194b. The parallel combination of a capacitor 197b and resistor 193b is connected between said diode and ground, resistor 193b being tapped off and connected to resistor 199b. Said power supply produces a half-wave rectified signal, the value of capacitor 197b being selected for minimum smoothing.

Driving circuit 30b operates as follows. When switch 42b is closed, a surge of energy is applied to crystals 189b and 188b and the motor 45b is set into oscillation. A signal representative of the frequencies of oscillation of said motor is reflected back through lines 204b and 203a b to the primary of transformer 212b. This signal is detected by the tuned circuit defined by secondary winding 210b and capacitor 214b, which is tuned to the desired frequency of oscillation of the motor. Only the portion of said detected signal representative of said desired frequency is transmitted to base 209b to switch transistor 205b on and off at an ultrasonic rate. When transistor 205b is on, the power signal from the power source, essentially in the form of a half-wave rectified signal, is short circuited. When transistor 205b is off, the power signal is applied through transformer primary winding 202b to the ultrasonic motor. In this manner, a driving signal consisting of bursts of ultrasonic oscillations repeated at a sonic rate are applied to motor 45b to produce bursts of ultrasonic vibrations repeated at a sonic rate.

Figures 16, 17:
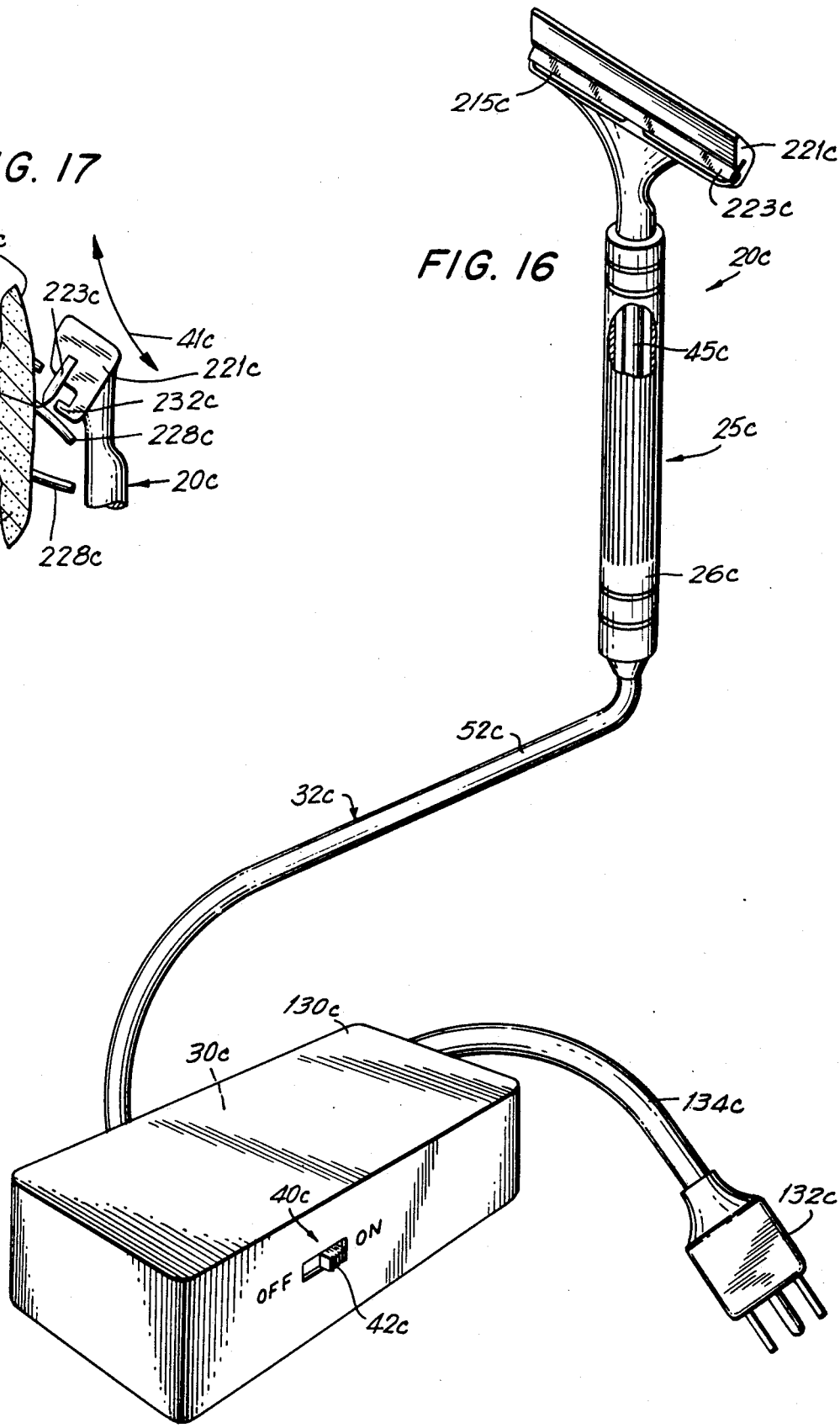
FIG. 16 is a perspective view of the invention as used for shaving.
FIG. 17 is the shaving apparatus in relation to the sin of the user.

Turning now to FIGS. 16 and 17, there is illustrated a shaving system 20c which is described in greater detail in the co-pending application assigned to the assignee of the present invention, Ser. No. 204,632, filed Dec. 3, 1971, and for present purposes, it is sufficient to indicate that it includes an instrument means or handle means 25c adapted to be held by the user in a conventional manner, with a detachable shaving head or assembly 221c containing a member or blade 223c to be ultrasonically vibrated and mounted therein. Extending from one end thereof is supply means 130c which supplies to the instrument means 25c, power from generator or power means 30c having an electrical cord 134c connected to a plug 132c adapted to be plugged into a standard electrical outlet; i.e. 60 cycles per second. Switching means 40c on the generator includees a switch 42c for providing power for energizing the ultrasonic transducer or motor 45c contained within the instrument casing or housing means 26c of the hand-held instrument 25c. The energy from the generator 30c is transmitted to the ultrasonic motor by wires extending through the flexible conduit 52c of the supply means 32c.

The complete asssembly for use in the home includes the generating means 30c, for example, a transistorized driving circuit means capable of producing a driving signal consisting of bursts of electrical oscillation at a frequency in the ultrasonic range, as defined herein, repeated at a sonic rate herein defined. Driving circuits to obtain the dual frequency are discussed in detail with respect to FIGS. 3, 14 and 15.

The ultrasonic energy available at the cutting edge 225c of the blade 223c provides several beneficial results. It has been found that, by reason of the vibrations at the cutting edge 225c, which vibrations may be in a substantially vertical plane; that is, in a plane perpendicular to the plane of the cutting edge 225c, the resistance of the blade member 223c across the skin surface is very substantially reduced. The friction reduction effects and the cutting ease may be obtained by the vibrations having an elliptical, orbital, longitudinal or flexural component of motion at the cutting edge 225c. A possible explanation of this observed phenomenon is that the extremely high acceleration of the cutting edge 225c of shaving member 223c resulting from the vibrations causes only a relatively small sliding friction to be present between the engaged skin surface and the shaving member 223c. Thus, the dual frequency provides a visible gross motion to the shaving member 223c and simultaneously imparts to the shaving member the acceleration forces to reduce the friction and successively subject the hair portions extending from the skin to the cutting action of the cutting edge at a repetition rate of from 15,000 to 500,000 times per second and thus provide a continuous severing of the hairs at or adjacent to the surface of the skin.

The frequency of the vibrations at the free end portion of blade member 223c is in the range from 15 to 500 kilocycles per second, while the amplitude of the vibrations is selected within the range from approximately 0.0001 to 0.025 inch so as to ensure the introduction of vibratory energy sufficient to perform the cutting of the hair particles and maintain the friction reduction qualities. Simultaneously therewith, the converter-motor system functions by cyclically interrupting the vibratory motion to produce the buzzing or jiggling which indicates that the razor is operating.

Thus, the vibratory energy applied at a suitable frequency, to the blade produces vibratory motion of the molecular structure of such blade so that the surface of blade 223c is continuously maintained, while being moved relative to the hair, at a state of microscopic motion in the ultrasonic range relative to the surface of the skin, whereby the frictional resistance of movement of the shaving member 223c to the surface is determined by the kinetic coefficient of friction therebetween rather than by the substantially larger static coefficient of friction between the material of the shaving member 223c and the skin. The ultrasonic shaving instrument 20c also permits a closer shave to be obtained due to the inherent characteristics of a vibratory member which when vibrated in the ultrasonic frequency range as herein defined will vibrate with an acceleration of at least 1,000g's such that the time of contact between the cutting edge 225c and the surface of the skin is minimal even when a static force is applied by the user against the skin.

Due to the geometric configuration of the mounting of the blade 223c within the shaving head assembly 221c, it is possible to obtain a flexural component of motion at the blade edge 225c and at the same time the physical vibration produced by the ultrasonic frequency produces peak accelerations in the showing member of the order of at least 1,000g. The ultrasonic frequency may be in the range of 20 KHz to 60,000 KHz and the low sonic frequency in the range of 0.1KHz to 0.10 KHz. Low guard edge 232c is designed to function in conjunction with blade edge 225c in effecting shaving. The ultrasonic vibrations are introduced in a longitudinal direction, and due to the geometry of the shaving head assembly 221c, the vibrations are induced in blade 223c in a plane substantially normal to the surface thereof.

CONCLUSION

From the foregoing, it will be evident that the application of bursts of ultrasonic vibrations repeated at a sonic rate is effective to provide significantly improved results in many applications of vibratory motion, only two of which have been herein illustrated by way of example. It is well appreciated that the invention herein defined may be employed in innumerable applications, some of which presently exist in the form of low frequency applications and others in the form of high frequency applications, so that for the first time, the synergistic benefits of the combination of hgih and low frequency effects may be achieved.

It will thus be seen that the objects set forth above, among those made apparent from the preceding description, are efficiently attained and, since certain changes may be made in carrying out the above method and in the devices set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An ultrasonic system for transmitting energy for performing work at a surface comprising:
    A. driving circuit means for producing a driving signal consisting of bursts of ultrasonic oscillations of a frequency in the range of 10KHz to 1,000KHz repeated at sonic intervals of a frequency in the range of 10Hz to 1,000Hz;
    B. ultrasonic instrument means adapted to be hand held by the user thereof including,
        1. a housing,
        2. an ultrasonic motor supported in said housing and electrically coupled to said driving circuit means for receiving said driving signal therefrom, said ultrasonic motor having a vibrating portion transmitting bursts of ultrasonic mechanical vibrations repeating at said sonic rate; and
        3. applicator means having at least a portion extending beyond said housing for engagement against said surface, said applicator means being mechanically coupled to said vibrating portion of said ultrasonic motor for receiving and transmitting said bursts of ultrasonic mechanical vibrations at said sonic rate, said ultrasonic instrument means being adapted so that sonic rate vibrations are tactilly detectable by a user holding said instrument means to provide an indication of the operation of the instrument means.

2. The system as defined in claim 1, wherein said vibratory means is elongated and the vibration is longitudinal.

3. The system as defined in claim 1, wherein said ultrasonic vibrations are in the range of 20 KHz to 60 KHz.

4. The system as defined in claim 1, wherein the physical vibration produced by said ultrasonic frequency produces peak accelerations in said vibratory means of the order of at least 1,000g.

5. The instrument as recitied in claim 1, wherein said driving circuit means includes first circuit means for producinng an oscillatory signal at said ultrasonic frequency; and second circuit means for amplitude oscillatory signal to produce said bursts of ultrasonic oscillations.

6. A driving circuit as defined in claim 1, wherein said second circuit means produces an essentially half-wave signal for such modulation.

7. The system as defined in claim 1, wherein said instruments means is a therapeutic instrument.

8. The system as defined in claim 1, wherein said motor includes a piezoelectric element capable of vibration at a plurality of frequencies including a desired frrequency, first circuit means for producing said ultrasonic vibrations; and second circuit means for modulating said ultrasonic vibrations at a sonic rate to produce a driving signal consisting of bursts of ultrasonic oscillations repeated at said sonic rate, said first circuit means comprising a power supply for producing a power signal; control means coupled to said power supply at a junction terminal for controlling the application of said power signal to said piezoelectric element as a driving signal; transformer means having a primary winding and a secondary winding, said primary winding being electrically coupled intermediate said junction terminal and said piezoelectric element for detecting a detected signal representative at least of the frequency of said driving signal; and tuned circuit means tuned to said desired frequency and formed from inductor means, capacitor means connected in parallel with said inductor means, said transformer means secondary winding defining said inductor means, said tuned circuit means being operatively coupled to said control means for actuating said control means at said desired frequency in response to said detected signal to produce said driving signal at said desired frequency.

9. The system as defined in claim 8, wherein said control means is a transistor means having an emitter, collector and base, said tuned circuit means being connected to said base for the control of the operation of said transistor means, the emitter-collector path of said transistor means being connected between ground and said junction terminal.

10. The system as defined in claim 8, wherein said second circuit means includes said power supply, said power supply being adapted to produce a power signal in the form of an essentially half-wave signal for such modulation.

11. The system as defined in claim 1, wherein said motor includes a piezoelectric element capable of vibration at a plurality of frequencies including a desired frequency, first circuit means for producing said ultrasonic vibrations; and second circuit means for modulating said ultrasonic vibrations at a sonic rate to produce a driving signal consisting of bursts of ultrasonic oscillations repeated at said sonic rate, said first circuit means comprising sensing means mechanically coupled to said transducer device for detecting the frequencies of vibration thereof and producing a detected signal representative of said frequencies of vibration; amplifier means having an input and an output; tuned circuit means tuned to said desired frequency and electrically connected intermediate said sensing means and said amplifier means input, said tuned circuit means being adapted to filter said detected signal and pass to said amplifier means input the component of said detected signal of said desired frequency; and means for operatively connecting said amplifier means output and said piezoelectric crystal for applying a driving signal to said crystal of said desired frequency.

12. The system as defined inc claim 11, wherein said sensing means is a piezoelectric sensing member mechanically coupled to said motor.

13. The system as defined in claim 12, wherein said second circuit means is adapted to produce an essentially half-wave signal for such modulation.

14. An ultrasonic system for transmitting energy for performing work at a surface comprising:
A. driving circuit means for producing a driving signal consisting of bursts of ultrasonic oscillations of a frequency in the range of 10KHz to 1,000KHz repeated at sonic intervals of a frequency in the range of 10Hz to 1,000Hz, said driving circuit means includes first circuit means for producing an oscillatory signal at said ultrasonic frequency; and the second circuit means for amplitude modulating said ultrasonic oscillatory signal to produce said bursts of ultrasonic oscillations at said sonic intervals;
B. ultrasonic instrument means adapted to be hand held by the user thereof including,
  1. a housing;
  2. an ultrasonic motor supported in said housing and having:
    i. piezoelectric transducer means electrically coupled to said driving circuit means for receiving said driving signal therefrom; and
    ii. a transmission member having a rear section mechanically coupled to said piezoelectric transducer means for receiving vibrations therefrom and a front section transmitting bursts of ultrasonic mechanical vibrations repeated at said sonic rate.
  3. applicator means having at least a portion extending beyond said housing for engagement against said surface, said applicator means being mechanically coupled to said transmission member front section for receiving and transmitting said bursts of ultrasonic mechanical vibrations at said sonic rate, sonic rate vibrations being transmitted to the hand of the user holding said instrument means to provide an indication of the operation of the instrument means; and
C. piezoelectric sensing means mechanically coupled to said transmission member for providing means for sensing variations in frequencies of said motor, said driving circuit means including means for maintaining said ultrasonic vibrations at a desired frequency in response to the signal produced by said piezoelectric sensing means.

15. An ultrasonic system as recited in claim 14, wherein said ultrasonic instrument means is in the form of a razor.

16. An ultrasonic system as recited in claim 14, wherein said ultrasonic instrument means is in the form of a toothbrush.

17. An ultrasonic system as recited in claim 14 including interchangeable means each adapted to be secured to the front end of said ultrasonic instrument means to permit a variety of applications of ultrasonic mechanical vibrations to a selected object for various results.

18. An ultrasonic system as recited in claim 17, wherein said interchangeable means are removably secured to the ultrasonic instrument means by threaded means.

19. The ultrasonic system as recited in claim 14, wherein said second circuit means includes an alternating power source; and half-wave rectifier means for producing a half-wave pulse signal for said modulation.

20. The ultrasonic system as defined in claim 14, wherein said first circuit means includes tuned circuit means tuned to a desired frequency for controlling the frequency of said driving signal, said ultrasonic instrument means being capable of vibration at more than one frequency including said desired frequency, and including means for applying to said tuned circuit means a detected signal representative of the frequencies of vibration of said instrument means, said tuned circuit means responding to the desired frequency portion of said detected signal to cause said driving signal means to produce a driving signal of said desired frequency.

21. An ultrasonic system as defined in claim 20, wherein said first circuit means includes a power supply for producing a power signal; switch means for controlling the transmission of said power signal as a driving signal to said ultrasonic instrument; and transformer means having a primary and secondary winding, said tuned circuit means including capacitor means connected in parallel with said secondary winding; said means for applying said detected signal including the primary winding and means for electrically coupling said power supply through said primary winding to said ultrasonic instrument means.

22. An ultrasonic system as defined in claim 20, wherein said means for applying said detected signal includes sensing means mechanically coupled to said ultrasonic instrument means for detecting the frequencies of vibration thereof, said first circuit means including amplifier means having an input and an output, said tuned circuit means being electrically connected between said sensing means and said amplifier means input and being adapted to filter said detected signal and pass to said amplifier means input the components of said detected signal of said desired frequency, said driving circuit means further including means operatively coupling said amplifier means output and said first connector for transmission of said driving signal.

23. An ultrasonic system as defined in claim 14, and further including power switching means operatively coupled to said driving circuit means and adapted to be selectively engaged by the user during operation of the system.

24. A system, as recited in claim 14, wherein said driving circuit means is adapted to produce spaced bursts of said ultrasonic oscillations.

* * * * *